United States Patent [19]
Schlueter, Jr. et al.

[11] Patent Number: 6,122,351
[45] Date of Patent: Sep. 19, 2000

[54] METHOD AND SYSTEM AIDING MEDICAL DIAGNOSIS AND TREATMENT

[75] Inventors: Edward L. Schlueter, Jr.; Paul A. DeSarra, both of Rochester, N.Y.

[73] Assignee: Med Graph, Inc., Rochester, N.Y.

[ * ] Notice: This patent is subject to a terminal disclaimer.

[21] Appl. No.: 09/392,117

[22] Filed: Sep. 8, 1999

Related U.S. Application Data

[63] Continuation-in-part of application No. 08/785,382, Jan. 21, 1997, Pat. No. 5,974,124.

[51] Int. Cl.$^7$ .......................... H04M 11/00; G06F 15/16; A61B 5/00
[52] U.S. Cl. ...................... 379/106.02; 709/203; 600/301
[58] Field of Search .................................. 379/106.02, 38, 379/93; 709/203; 600/300, 301; 283/76

[56] References Cited

U.S. PATENT DOCUMENTS

| | | |
|---|---|---|
| 4,632,428 | 12/1986 | Brown . |
| 5,199,439 | 4/1993 | Zimmerman et al. . |
| 5,390,238 | 2/1995 | Kirk et al. .......................... 379/106.02 |
| 5,558,638 | 9/1996 | Evers et al. . |
| 5,594,638 | 1/1997 | Iliff . |
| 5,633,910 | 5/1997 | Cohen ....................................... 379/38 |
| 5,692,073 | 11/1997 | Cass . |
| 5,704,364 | 1/1998 | Saltzstein et al. ...................... 600/300 |
| 5,974,124 | 10/1999 | Schlueter, Jr. et al. ............ 379/106.02 |

*Primary Examiner*—Zarni Maung
*Assistant Examiner*—Tammy Tak-kam Lee
*Attorney, Agent, or Firm*—Harris Beach & Wilcox, LLP

[57] ABSTRACT

A method and system that assists medical practitioners who treat or prescribe treatment of patients having a medical condition which requires long-term profiling of medical data taken from the patient's body. Medical practitioners, their assistants, and patients take medical readings of predetermined medically important variables. These readings are stored as raw data in a data receptacle such as a smart card or in a portable medical instrument, then input into a remote computer, or the raw data is manually entered into a remote computer. The remote computer then connects with a primary computer using a communications connection and transmits the raw data to the primary computer system which maintains a database of patients and their medical readings. The communications connection can be any means of connecting two computers for communication therebetween but is preferably an Internet connection wherein the remote computer is operated as a web client and the primary computer is operated as a web server. The readings can also be transmitted to the primary computer using an ordinary telephone to call a telephone peripheral which can receive the raw data using automated speech recognition or touch-tone recognition. Requests for data by medical practitioners is transmitted to the primary computer in a manner similar to the transmission of raw data. In response to a request for data, output, in the form of a chart or graph, or multiple charts and graphs, is transmitted to the remote computer for display on the computer screen and/or printed for hard copy, or faxed to the medical practitioner or assistant.

1 Claim, 4 Drawing Sheets

| DATE | DAY | 7am | 10am | 1pm | 3pm | 5pm | 7pm | 10pm |
|---|---|---|---|---|---|---|---|---|
| 8/17 | | 133 | | | | | 79 | |
| 8/18 | | 119 | | | | | 211 | 106 |
| 8/19 | | 110 | | | | 85 | | 101 |
| 8/20 | | 157 | | | | 125 | | 189 |
| 8/21 | | 143 | | | | | 115 | 143 |
| 8/22 | | 126 | | | | 120 | | 152 |
| 8/23 | | 134 | | | | 219 | | 258 |
| 8/24 | | 184 | | | | 207 | | 180 |
| 8/25 | | 147 | | | | 148 | | 304 |
| 8/26 | | 119 | | | | 113 | | 227 |
| 8/27 | | 156 | | | | | 267 | 182 |
| 8/28 | | 145 | | | | | 126 | 125 |
| 8/29 | | 158 | | | | 173 | | 203 |
| 8/30 | | 135 | | | | | 160 | 227 |

*FIG. 2*

METHOD AND SYSTEM AIDING MEDICAL DIAGNOSIS AND TREATMENT

This application is a continuation-in-part of application 08/785,382 filed Jan. 21, 1997, now U.S. Pat. No. 5,974,124

BACKGROUND

Medical symptoms of many types of conditions can be difficult to detect by medical professionals if they occur over an extended period of time. Currently, medical diagnostics such as blood pressure readings and glucose readings are taken at doctors' offices or blood laboratories. The readings are then collected manually and depend on the patient's state of health at that particular time. In some cases, individuals take home readings to assist doctors to better determine medication identification and levels. This data depends on the patient's proficiency and accuracy at taking readings, and is hard for the physician to analyze and is normally communicated only at a doctor's visit. Typically, the patient is diagnosed and medicated based on a minimum amount of data and analysis, which furthermore is not presented to the doctor in a format that facilitates diagnosis. Each reading is presented by a lab report on a separate page, or by an individual manually listing out his own readings with the date and time that these readings are taken—often in irregular intervals.

Diagnosis of many types of medical conditions, such as hypertension, hypoglycemia, obesity, diabetes mellitus, or any disease or condition that requires long-term profiling of one or more variables such as pulse rate, blood pressure, percent body fat, glucose level, cholesterol level, white blood cell count, T-cell count, etc. to effectively diagnose and treat can be markedly improved by a system to consolidate the data and present the data in a format which facilitates such diagnosis.

For the purpose of illustration, consider the condition known as diabetes mellitus, which is a common form a diabetes characterized by inadequate secretion or utilization of insulin, a hormone that regulates blood-sugar levels in the body. According to research done by the Centers for Disease Control and Prevention, in 1989 there was approximately 6.7 million individuals who reported having diabetes mellitus, and it was estimated that an equal number had the condition, but were unaware of it. Diabetes mellitus results in excessive urine production, thirst, hunger, and loss of weight, and can be very disruptive of a person's life. This condition is treatable, but proper treatment depends on accurate long-term profiles of a patient's blood sugar levels. In addition, people who suffer from diabetes mellitus are also at increased risk for heart disease, and should monitor their heart rate and blood pressure at regular intervals. Doctors working with diabetes patients must inspect a great deal of data associated with tracking the disease. Diabetes patients often measure the blood sugar level two, three, four, or five times a day. Patients typically will take their own blood-sugar level readings using a hand-held medical instrument, and record the readings by writing the results on a chart, which is presented to the medical practitioner during a scheduled appointment.

Medical practitioners, who are increasingly working with more patients with fewer time devoted to each patient, simply do not have time to carefully review a stack of hand-written record sheets to determine whether a patient's recent readings are significantly improved in comparison to the patient's previous readings. The present invention addresses this problem by providing accurate records with simple and versatile input and output of the information from a centralized data base. Trends are easily spotted, as are erratic or cyclic readings. Thus, diagnosis and treatment of a disease such as diabetes mellitus becomes quicker and more accurate for improved results.

SUMMARY

The purpose present invention is to target individuals who potentially have a medical condition such as diabetes mellitus and are unaware of it, and to improve diagnosis and treatment by making it more accurate and to assist medical practitioners in determining the proper amount of medication or other treatment to prescribe. The term medical practitioner is intended to include any individual who treats, or prescribes treatment to another individual to improve the latter's health or well-being. The focus of this invention is to gather, organize, and present data which is collected over a long period of time in a way that best facilitates accurate diagnosis and proper treatment of such medical conditions which require long-term profiling of medical readings.

In order to accomplish this goal, data must be gathered, stored, and available to the medical practitioner at their convenience. Medical data is gathered in a variety of ways. Medical practitioners, their assistants, laboratories, and patients themselves are often involved in taking medical readings of such things as blood pressure, pulse rate, weight, and bloodsugar level. Of course, the invention can accommodate any medically important variable. Once the data is gathered, it must be added to a database for storage, such that it is available for use when required by a medical practitioner.

Medical readings taken in the medical practitioners offices and laboratories are uploaded to a centralized database either via a common network, over telephone lines, or over the Internet. Alternatively, the information could be stored in a network server in a common LAN or fiber optic network if available, e.g. in hospitals and HMOs, which often have their own dedicated computer networks to connect their administrative offices, laboratories, and doctor offices, and on which their patient medical records are stored. In the case of private practices, the Internet could be used, with adequate security precautions taken to prevent unauthorized access to the information, or the information could be uploaded directly to a computer system acting as a database server via modem-to-modem communication over telephone lines.

Patients who take their own readings do so either using their own portable devices or they use equipment set up for their use in drug stores and grocery stores. Examples of such equipment include heart rate and blood pressure reading machines which are commonly found in such places.

Many of the portable medical devices are capable of storing medical readings along with the time and date of the reading. This information can then be downloaded directly into a computer. A medical practitioner or medical assistant can perform this step when the patient visits his medical practitioner. Alternatively, the portable medical device may be constructed to transmit the information to a computer via the telephone network, which a patient can accomplish by plugging the device into an ordinary telephone jack or a separate interface unit which is connected to a telephone jack.

Medical instruments set up for public use normally display the result. These machines can be modified or replaced with upgraded machines to automatically send the information directly into the database, or into a "smart card" (or other data receptacle) which the patient can present to the medical practitioner upon his visit, or which the patient may insert into a reader in his home for downloading the information and transmitting it to the primary computer via the telephone network.

Once a remote computer in the medical practitioner's office contains the most recent data, it must be uploaded to the primary computer system and added to the previously collected data. Once in the primary computer system, the data is processed and made available to the medical practitioner to make diagnoses or establish progress.

The data can also be input directly into the primary computer if the patient agrees to "phone in" his results each time he takes a reading either to a receptionist who manually puts the information into the primary computer system or using a touch-tone phone or a system with voice-recognition software to input the data into the database in the primary computer using an automated system with such capabilities.

While presenting a medical practitioner with a smart card or other data receptacle is an improvement over the current technique for providing a practitioner with medical data, i.e., presenting the practitioner with forms filled out by hand, a significant advantage may be had by providing a patient with means to instantly transmit the data from his or her home to the medical practitioner. In particular, the medical practitioner is provided with the means to review the patient's up-to-date record without the patient having to visit the office of the practitioner. Instead, the practitioner merely access a data base having the patient's records, and can view them at his leisure in a graphical form.

If a patient is unwilling or unable to take his own medical readings, a medical practitioner or assistant can visit the patient's residence, take the required readings, and input the data into the primary computer system, either directly or through the use of a remote computer.

Once the information is present in the database, all the medical practitioner needs to do is access the information via a network, telephone, or Internet connection and software capable of presenting processed data in a format that facilitates diagnosis, such as a graph or a chart.

By virtue of the foregoing process, medical practitioners' needs relating to hard-to-identify chronic medical conditions and medical conditions which depend on long-term profiling for proper treatment are effectively met.

BRIEF DESCRIPTION OF THE DRAWING

FIG. 2 shows a portion of an example of a chart that can be useful to medical practitioners in aiding diagnosis and treatment of diabetes mellitus.

DETAILED DESCRIPTION OF THE PREFERRED EMBODIMENT

Figure 1:
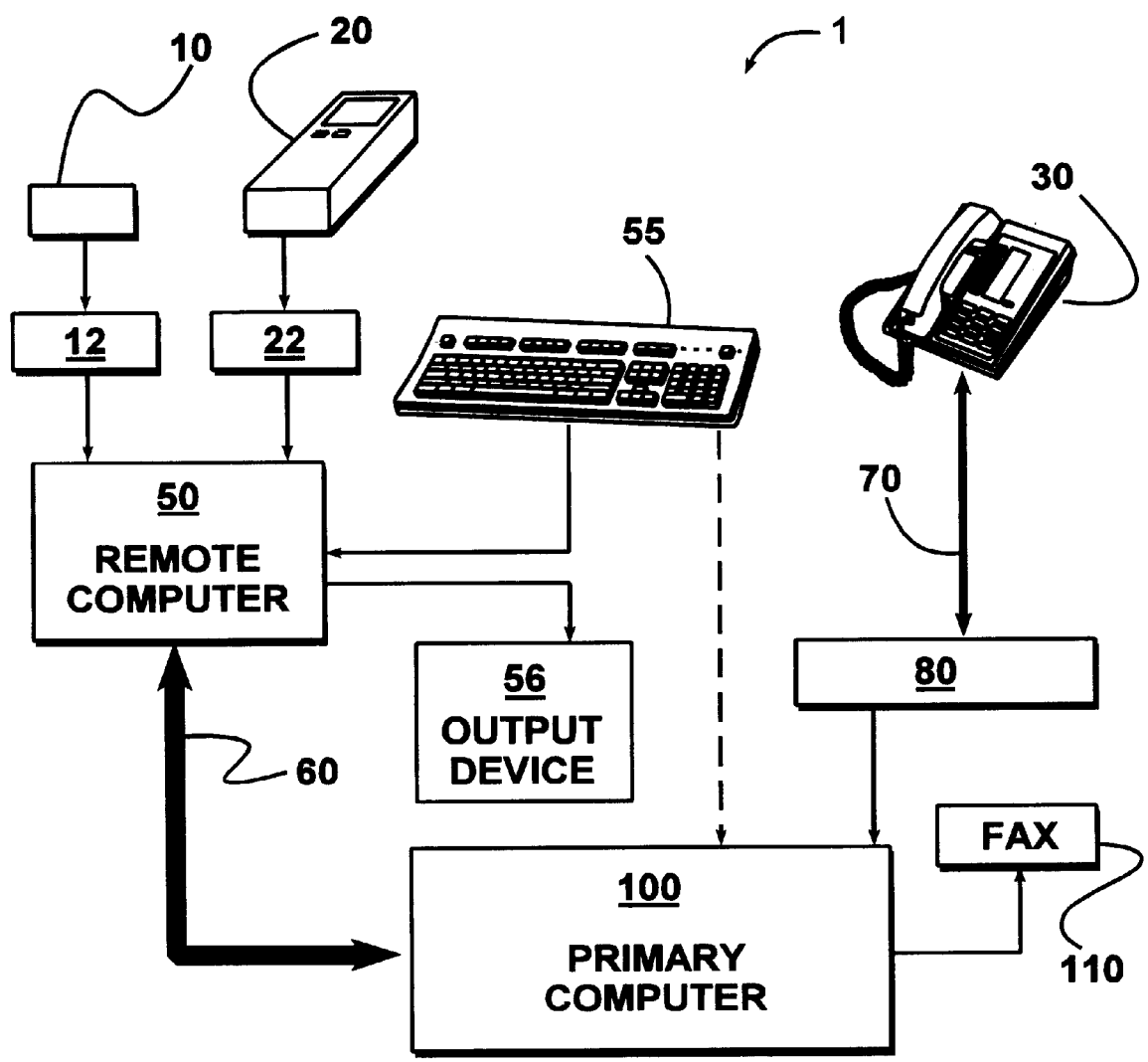
FIG. 1 shows a preferred embodiment of the system of the invention.

The invention, which is discussed below in reference to FIG. 1, consists of a system and method for assisting physicians in accurately diagnosing and treating medical conditions which require long-term profiling of each patient's condition. As a system, the invention comprises computer hardware and software, configured for use as a database capable of storing medical information, especially long-term profiles of medical conditions, of any number of patients, and processing and supplying the information to physicians in a manner which facilitates diagnosis and treatment of conditions from which the patients may suffer.

The computer system 1 includes of data input means, data process and storage means, and data output means. Data input means are adapted for manual or automated data collection from sources including medical offices, laboratories, and patients. Computerized data can be transmitted from these remote locations via telephone lines using direct modem-to-modem communication or by an Internet connection, whereby the database operator will collect data through implementation of a user-friendly graphical user interface over the World Wide Web. Alternatively, individual patients can upload their data on a regular basis by calling a special phone number, and either by operating their touch-tone phone, or using voice recognition software, input the information to the database through a telephone interface. A low-tech substitute for this would be to employ a receptionist to take phone calls and manually input the information into the database. Patients who fail to report their readings at their scheduled intervals can be automatically reminded by phone by calling or paging them using the telephone interface. These methods are described in greater detail below.

There are five main avenues contemplated for inputting data into the primary computer 100. The first avenue is by manually entering data from medical readings into a remote computer 50 using keyboard 55. The remote computer 50 is programmed to then automatically access the primary computer 100 and transmit the data to the primary computer 100 via connection 60. This operation is performed in laboratories and medical practitioners' offices, or by patients who take their own readings and own computers capable of accessing the host computer system 100. Additionally, if a patient is unable to make regular trips to a medical practitioner's office or laboratory, and is unable or unwilling to take their own medical readings, a medical practitioner or assistant can visit the patient's home and collect the data, and manually enter the data into a remote computer system 50 to be transmitted to the primary computer system via connection 60. Connection 60 includes any means of connecting one computer to another for purpose of communication.

If the remote computer and the primary computer are not commonly owned, the connection can be a direct modem-to-modem connection over telephone lines or an Internet connection. If the former connection is used, the primary computer is configured as a dial-up host. In the latter case, the primary computer is operated as a web server on the World Wide Web, and can be accessed through the Internet. The user accesses a web page on the primary computer and enters data in a form which is displayed on the remote computer's screen. The data is then sent to the primary computer, which can then store the information in its database. The primary computer can operate as both a dial-up server and a web server simultaneously.

Connection 60 can also be a direct network connection, which may be desirable if the medical laboratory or medical practitioner's office is located in a larger medical institution which owns and operates the primary computer system.

The second avenue of data input relies on data receptacle 10, which may include any device capable of storing data readable by a computer peripheral 12. It is contemplated that data receptacle 10 could take the form of a "smart card" of a size and shape that would be convenient for the patient to carry in a wallet or purse. Data is encoded in the data receptacle 10 using medical instruments (not shown) equipped for such a task. It is contemplated that heart rate and blood pressure machines commonly found in drug and grocery stores will be so equipped. Once a week, or whenever prescribed, the patient visits the location having such a machine that is convenient to the patient, and the readings are taken by the machine and encoded on the smart card. When the patient visits his medical practitioner, he merely presents the data receptacle 10 which has all the recent readings with associated date and time to the medical practitioner or assistant, who then inputs the data from the data receptacle 10 to the remote computer 50 using data receptacle reader 12 which converts the data into a form usable by the remote computer 50. Data is then transmitted to the primary computer 100 as discussed above with reference to the first avenue.

Figure 1A:
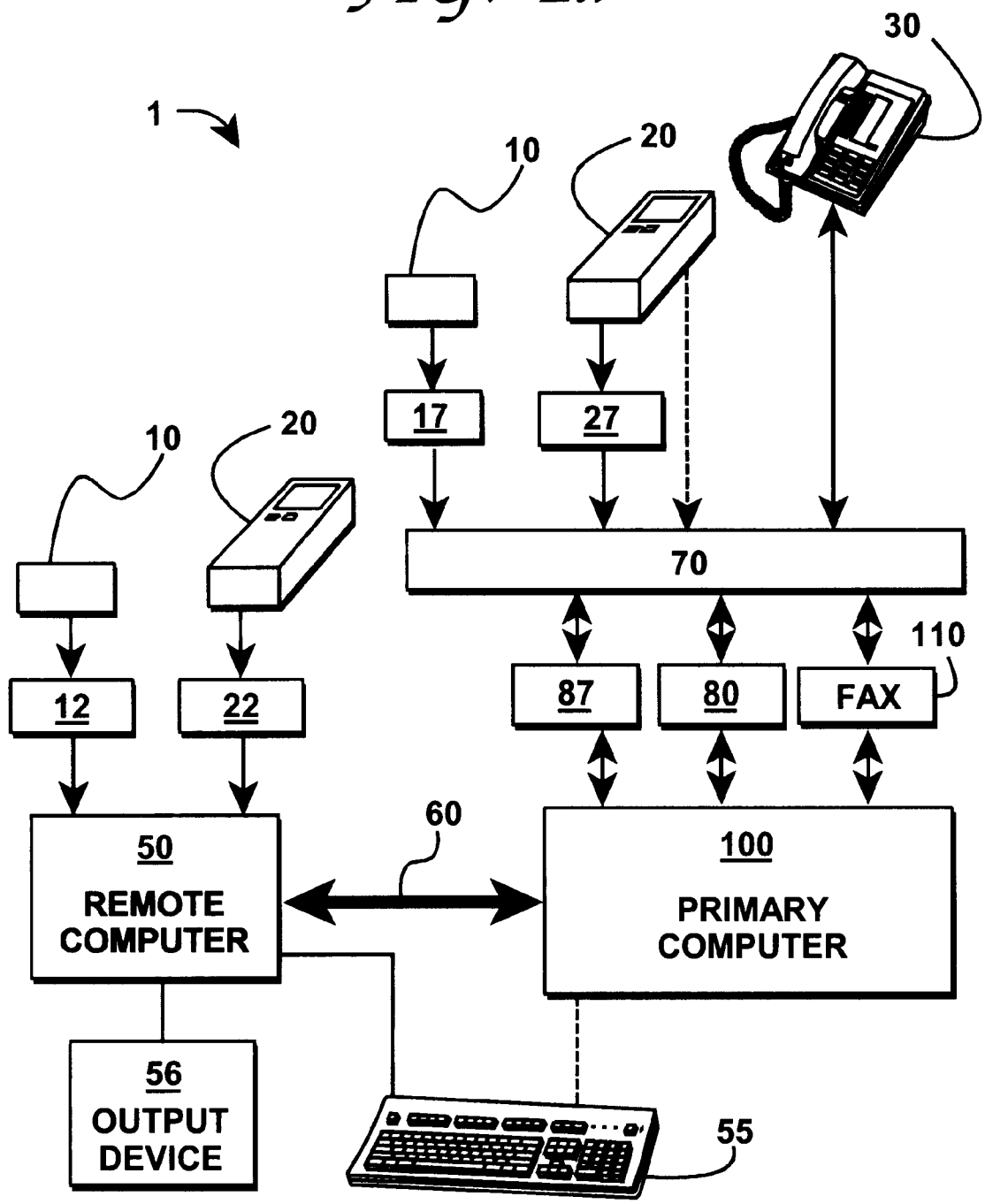
FIG. 1a shows additional features of the invention.

Alternatively, the patient may be provided with a data receptacle reader 17, as shown in FIG. 1a, which is connected to the telephone network 70 via an ordinary phone jack in the patient's home. Data receptacle reader 17 will then automatically read the data stored in data receptacle 10 and transmit the information to primary computer 100 via modem 87 and telephone network 70.

The third avenue of data input employs portable medical instrument 20. Portable medical instruments 20 are capable of taking readings such as blood pressure or blood sugar level and storing the readings in its own memory and then passing the stored data to a personal computer. In this respect, portable medical instrument 20 is much like data receptacle 10. Data passes to remote computer 50 through interface 22. Data is then transmitted to the primary computer 100 as discussed above with reference to the first and second avenues of data input.

As with the data receptacle 10, it is contemplated that portable medical instrument may be operated via interface 27 to transmit the data stored in portable medical instrument 20 to the primary computer 100 via telephone network 70. Alternatively, portable medical instrument may be equipped with a built-in telephone interface and thereby access the telephone network 70 without requiring a separate interface 27. Either interface 27 or portable medical instrument 20 will automatically read the data stored in portable medical instrument 20 and transmit the information to primary computer 100 via modem 87 and telephone network 70.

The fourth and fifth avenues of input rely on the individual or third person taking the medical readings and calling the medical readings in to be entered into the data base on the primary computer 100. In the fourth avenue of data input, this is accomplished by employing a receptionist to take phone calls and manually taking the medical readings over the phone, and manually typing the data using keyboard 55 into the remote computer 50 (or directly into the primary computer 100 if keyboard 55 is connected to the primary computer 100 as represented in FIG. 1 by the dashed lines extending from the keyboard 55 to the primary computer 100). In the fifth avenue of data input, the individual taking the medical readings phones-in the results using telephone 30 to call primary computer telephone interface 80 via telephone lines 70. The telephone interface 80 is capable of automatically answering the phone, and prompting for, and accepting the necessary medical information by using a touch-tone phone or by using speech-recognition software, then converting that information into a form usable by the primary computer 100 to which telephone interface 80 is connected.

If the patient is taking his own readings and forgets to call the results in (or forgets to take the readings) the primary computer 100 is capable of calling or paging the patient using telephone interface 80 to remind him.

All five avenues of data input can operate concurrently in a single system which is designed to fill every customer's need, including both patients and medical practitioners. It is also to be understood that any number of remote computers 50 can be configured to access primary computer 100, and that only one remote computer 50 is shown in FIG. 1 for illustration purposes only. Similarly, the primary computer may have any number of ports for accepting data from remote computers and any number of telephone interfaces for taking phone calls, and it is only for illustration purposes that FIG. 1 shows only one input port (where connection 60 meets primary computer 100) and only one telephone interface 80. The system 1 can thus accommodate a large population of patients under a variety of circumstances having a variety of needs and capabilities.

The primary computer 100 is a multi-purpose computer having software and hardware that enable it to receive information from the variety of sources mentioned, a microprocessor to process the data, store the data on a mass storage device integrated with the computer 100, and present the raw and processed data when required via output means. Its primary purpose is to receive medical readings over long periods of time, store the information as medical histories in a data base application, and present the information to medical practitioners in a form which facilitates accurate diagnosis and treatment of patients' chronic medical conditions.

The received, or raw, data consists of individual readings or measurements of medically-important variables of patients. Obviously, different patients may be measuring different parameters, or variables. One patient might be measuring heart rate and blood pressure, another body weight or body fat, and a third blood sugar, depending on the needs prescribed by the medical practitioner involved. Each reading is combined in a relational data base, or other type of data base, with that patient's previous readings. These readings are then available to the medical practitioner by the output means to be discussed in further detail below. The primary computer will also perform calculations to the data to provide useful statistics to the medical practitioner. For example, data can be averaged on a daily, weekly, bi-weekly, or monthly basis. Morning readings can be averaged together, and evening readings can be averaged together. These averaged can be calculated as needed, then plotted on a graph to facilitate a clear understanding on the part of the medical practitioner of the trends in the data or whether data is erratic or steady.

There are two methods medical practitioners can get useful information from the database on the primary computer 100 to their remote location. The first method is to access a remote computer 50 located, for example, in the medical practitioner's office, which can download information from the primary computer 100 through connection 60. Again, connection 60 can include a direct network connection, a modem-to-modem connection, or an Internet connection. In the latter case, the remote computer, using software commonly referred to as a "web browser," such as Netscape, Mosaic, or Internet Explorer, can access the primary computer 100, which would be set up as a "web server." Remote computer 50 is provided with software enabling automatic access, retrieval, and display of the required information at the request of the user—typically the medical practitioner or assistant.

The second method is provided for medical practitioners who do not have personal computers at their disposal which are capable of connecting to the primary computer 100. In such cases, the medical practitioner or assistant will call, using telephone 30, telephone interface 80, and, using either the telephone touch-tone pad or speech recognition, make a request for a medical report on a specific patient. This information is then faxed directly to the medical practitioner's office using fax machine 110.

As can be seen, FIG. 1, on the left, shows the "high-tech" utilization of the invention, where the right side of FIG. 1 shows the "low-tech" utilization of the invention. The main distinction between the two systems is that on the high-tech side, the patient or physician using the system requires a computer for data input and output, whereas on the lowtech side, the patient only requires a telephone to call in the readings and the physician only needs a telephone to make a request for data, and a fax machine to receive the chart or graph.

In an example of applying the invention, a patient was diagnosed with diabetes mellitus and is asked by his doctor to take three blood sugar level readings a day: Once in the morning, once before dinner, and once before bed. These readings were taken by the patient and recorded in a primary computer system via a keyboard. A chart was generated, a portion of which is shown as FIG. 2. The chart shows each reading taken with the approximate time for each reading identified by the column in which the reading appears. This is a common type of chart normally employed by patients who manually record their readings, however the computer is programmed to automatically pick out high and low readings and highlight them by displaying the reading in a colored box, as represented in the drawing by the shaded boxes. High readings are highlighted red, and low readings are highlighted green. The remaining readings are displayed in yellow boxes. These colors are, of course, only exemplary, and any color which distinguishes high and low readings would serve the function. Additionally, rather than placing the readings in discrete boxes, the readings can be placed along a continuum for more accurately visualizing the exact time each reading was taken.

Figure 3:
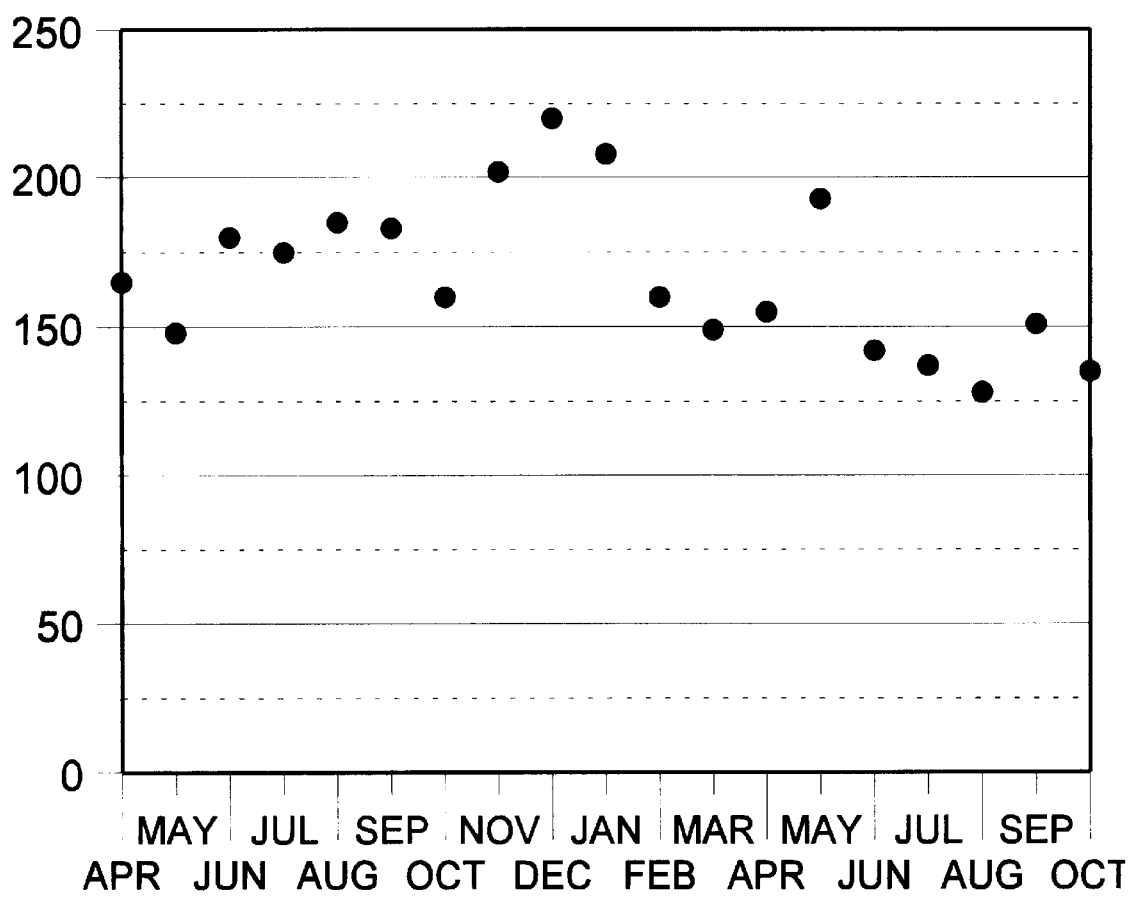
FIG. 3 shows an example of a graph that can be useful to medical practitioners in aiding diagnosis and treatment of diabetes mellitus.

The readings for each month were then averaged together and plotted on a graph shown in FIG. 3, which plots months beginning in April of 1995 and ending in October of 1996.

As can be seen, the glucose level is erratic and generally rises until January of 1996, where corrective action was taken, resulting in a general decline of glucose level in the blood.

As the example shows, the invention enables medical practitioners to quickly and easily spot trends and track the progress of patients they are treating without requiring excessive "extra steps" on the part of medical practitioners employing this invention.

Having substantially described the invention, it is understood that the scope of the invention is limited not by the specification above, but by the appended claims.

We claim:

1. A method for improving and facilitating diagnosis and treatment of patients having medical conditions requiring long-term profiles of specific variables, said method including the steps of:

using at least one measuring device, periodically taking a measurement of at least one medically important variable that has been identified for a patient from a body of said patient;

ensuring said patient is separated from said at least one measuring device after taking each said measurement;

inputing said at least one medically important variable as raw data into a primary computer system after said step of ensuring said patient is separated and recording said raw data in a mass storage device integrated with said primary computer system;

compiling said raw data as data for said patient using the primary computer system, said data representing a history of values for said at least one medically important variable for said patient;

receiving a request for data of one of said patients from by a medical practitioner that is treating said one of said patients; and outputting requested data for said one of said patients in the form of at least one of a chart and a graph to said medical practitioner;

said step of inputting comprising one of:

transferring electronically said raw data from said measuring device to said primary computer using an automated telephone interface, without the manual input of said data;

transferring electronically said raw data from said measuring device to a data receptacle, then transferring electronically said raw data from said data receptacle to said primary computer using an automated telephone interface, without the manual input of said data; and transferring electronically said raw data from said measuring device to a data receptacle, then transferring said raw data from said data receptacle to a remote computer, without the manual input of said data then transferring said raw data from said remote computer to said primary computer system.

\* \* \* \* \*